(12) United States Patent
Usui et al.

(10) Patent No.: US 6,414,204 B1
(45) Date of Patent: Jul. 2, 2002

(54) PROCESS FOR PRODUCING ALLYL CHLORIDE

(75) Inventors: Kenji Usui, Kawasaki; Shoichi Oishi, Shinnanyo; Toshitaka Hiro; Tatsuharu Arai, both of Kawasaki, all of (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/783,329

(22) Filed: Feb. 15, 2001

Related U.S. Application Data
(60) Provisional application No. 60/258,559, filed on Dec. 29, 2000.

(30) Foreign Application Priority Data

Feb. 15, 2000 (JP) ........................................ 2000-041417
Jan. 31, 2001 (JP) ........................................ 2001-024257

(51) Int. Cl.$^7$ ............................................. C07C 17/00
(52) U.S. Cl. ..................................... 570/217; 570/258
(58) Field of Search ................................. 570/217, 258

(56) References Cited

U.S. PATENT DOCUMENTS 5,196,611 A * 3/1993 Henkelmann et al. ...... 570/217
5,384,415 A * 1/1995 Mas et al. .................. 570/258

FOREIGN PATENT DOCUMENTS

JP          62-286936          12/1987

* cited by examiner

*Primary Examiner*—Alan Siegel
(74) *Attorney, Agent, or Firm*—Sughrue Mion, PLLC

(57) ABSTRACT

In a process for production of allyl chloride whereby allyl alcohol and hydrogen chloride are reacted in the presence of a catalyst and the resulting allyl chloride is distilled off from the reaction system, the by-production of diallyl ether is suppressed by lowering the molar concentration ratio of hydrogen chloride with respect to allyl alcohol in the reaction solution ($[AAL]^{1/2}/[HCL]$).

6 Claims, 1 Drawing Sheet

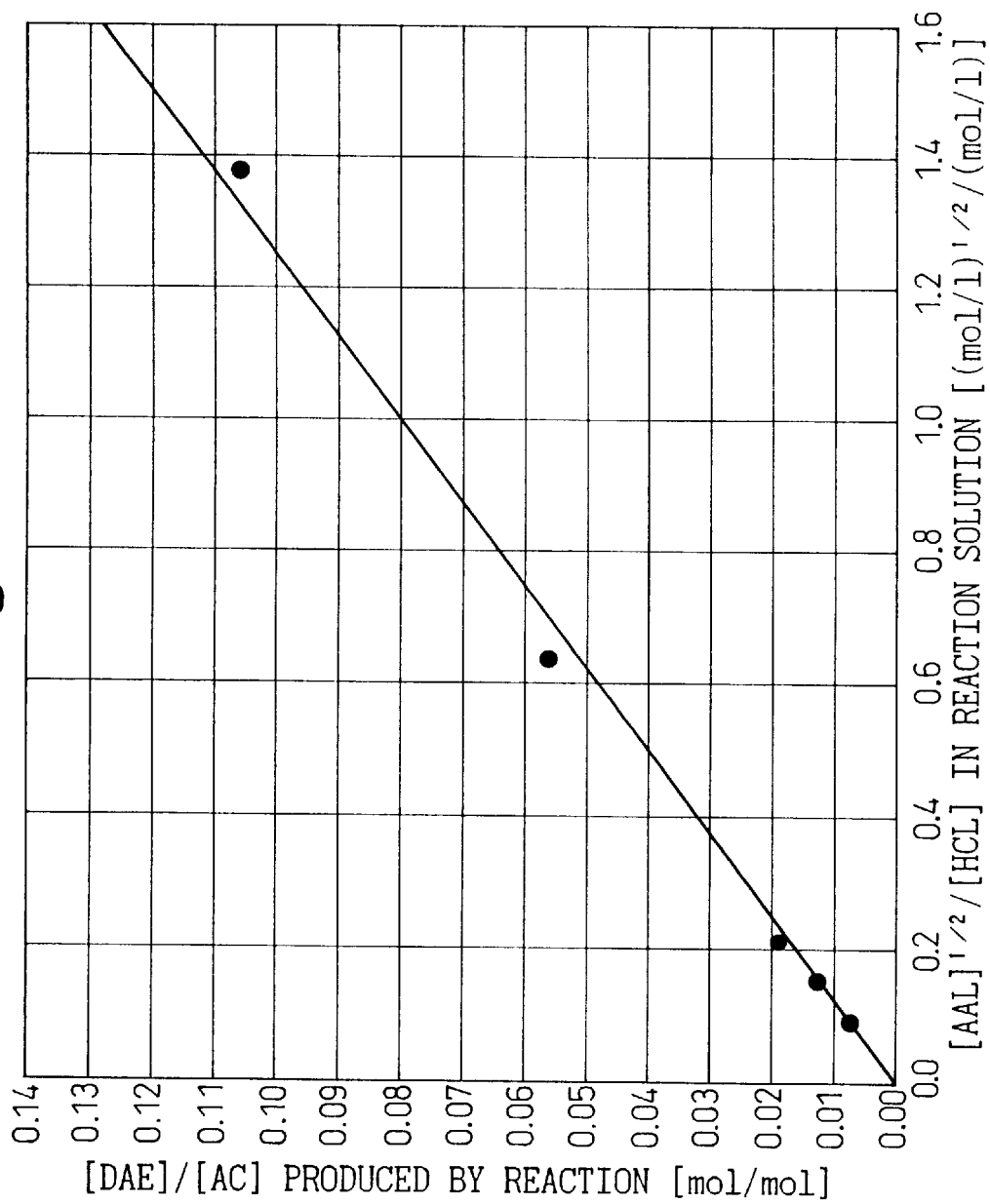

PROCESS FOR PRODUCING ALLYL CHLORIDE

CROSS-REFERENCE TO RELATED APPLICATIONS

This application is an application filed under 35 U.S.C. §111(a) claiming benefit of the filing date of the Provisional Application 60/258,559 filed Dec. 29, 2000, pursuant to 35 U.S.C. §111(b).

BACKGROUND OF THE INVENTION

1. Field of the Invention

The present invention relates to an allyl chloride production process. Particularly, the invention relates to a process whereby allyl alcohol and hydrogen chloride are reacted to produce allyl chloride, an important compound used as an allyl compound starting material for epichlorohydrin, glycerin and the like, as a starting material for agricultural chemicals such as herbicides and pesticides, as a starting material for medicines such as sedatives and anesthetics, as a starting material for aromatics, as a soil enhancer, etc.

2. Description of Related Art

Allyl chloride (sometimes abbreviated hereunder as "AC") has conventionally been produced by chlorination of propylene. This production process, however, has serious drawbacks when employed as an industrial production process, including:

1) a high reaction temperature and production of various by-products,
2) carbonization of polymer by-products of the reaction, and clogging of reactors,
3) severe corrosion of the apparatuses due to the high temperature at which hydrogen chloride is handled, and
4) production of chlorinated organic by-products that tend to be harmful to the environment.

A method has been reported for a more industrially advantageous production of allyl chloride, whereby allyl alcohol (sometimes abbreviated hereunder as "AAL") and hydrogen chloride (sometimes abbreviated hereunder as "HCL") are reacted in the presence of copper (I) chloride to synthesize allyl chloride (Jacques J., Bull. Soc. Chim. Fr., [5] 12, 843 (1945)). In this method, however, the reacted solution separates into an organic phase and an aqueous phase, with allyl chloride as well as a large amount of diallyl ether (sometimes abbreviated hereunder to "DAE") and a small amount of unreacted allyl alcohol mixed in the organic phase, and the allyl chloride yield is only about 70 wt %, which is industrially unsatisfactory.

The inventors have proposed, in Japanese Examined Patent Publication No. 6-92329, a process for production of allyl chloride whereby allyl alcohol and hydrogen chloride are reacted in the presence of a catalyst, and the allyl chloride produced is distilled off from the reaction system as the reaction progresses. This process suppresses production of diallyl ether as a by-product of the reaction, in order to give a high yield of allyl chloride.

For economic industrial application of this process, the reaction is preferably carried out in a continuous manner. "Continuous" means that the allyl alcohol and hydrogen chloride starting materials are continuously supplied to the reaction system, and the produced allyl chloride is continuously distilled off from the reaction system. However, since the allyl alcohol starting material will be distilled off under conditions in which the water by-product is distilled off from the reactor continuously along with the allyl chloride, it is difficult to evaporate and distill off the water from the reaction system.

For this reason, Japanese Examined Patent Publication No. 6-92329 teaches that the reaction solution may be drawn out and the excess water distilled off before it is returned to the reactor, but it discloses no concrete method for doing so. It is also mentioned that the distilled allyl chloride contains hydrochloric acid, and that this is therefore washed with weak alkali water before purifying the allyl chloride, but this method poses another problem of production of salts during the allyl chloride purification process. Another problem with the process described in Japanese Examined Patent Publication No. 6-92329 is that a high reaction temperature results in a greater amount of diallyl ether by-product.

BRIEF SUMMARY OF THE INVENTION

It is an object of the present invention to provide a process for production of allyl chloride whereby allyl alcohol and hydrogen chloride are reacted in the presence of a catalyst and the resulting allyl chloride is distilled off from the reaction system, which process both suppresses production of diallyl ether as a by-product and continuously produces allyl chloride.

As a result of diligent research aimed at achieving the aforementioned object, the present inventors have completed the present invention upon the discovery that in a process for production of allyl chloride whereby allyl alcohol and hydrogen chloride are reacted in the presence of a catalyst and the resulting allyl chloride is distilled off from the reaction system, the production of the diallyl ether by-product can be suppressed by lowering the molar concentration ratio of HCL with respect to allyl alcohol in the reaction solution ($[AAL]^{1/2}/[HCL]$).

In other words, the present invention relates to the following [1] to [8].

[1] An allyl chloride production process that comprises a) a step of supplying allyl alcohol and hydrogen chloride to a reactor and reacting them to produce allyl chloride and water, b) a step of distilling off the produced allyl chloride from the reaction system in a vapor phase and recovering it, c) a step of drawing out the reaction solution from the reactor, d) a step of distilling off and separating the water from the drawn out reaction solution, and e) a step of returning, back to the reactor, the remaining solution containing the hydrochloric acid and catalyst from which the water has been distilled off and separated.

[2] An allyl chloride production process whereby allyl alcohol and hydrogen chloride are reacted in the presence of a catalyst and the resulting allyl chloride is distilled off from the reaction system, wherein the allyl chloride production process comprises conducting the reaction in a range of 80–120° C. and supplying the allyl alcohol and hydrogen chloride such that the molar concentration ratio of the allyl alcohol and hydrogen chloride in the reaction solution is no greater than 0.2 in terms of $[allyl\ alcohol]^{1/2}/[hydrogen\ chloride]$.

[3] The process of [2] above, wherein the organic phase containing the distilled allyl chloride is separated from the aqueous phase, and the organic phase is distilled off after extraction using water.

[4] The process of [2] or [3] above, wherein at least a portion of the aqueous phase separated from the organic phase and/or an aqueous extract of the organic phase is returned to the reactor.

[5] The process of any of [2] to [4] above, which further comprises the following three steps.

(1) A step of drawing out the reaction solution from the reactor.

(2) A step of distilling off and separating the water from the reaction solution obtained in step (1).

(3) A step of returning to the reactor the remaining solution containing the hydrochloric acid and catalyst, obtained in step (2).

[6] The process of [5] above, wherein during distillation and separation of the water in step (2), the fraction with a lower boiling point than water is recovered and at least a portion of this fraction is returned to the reactor and/or the allyl chloride purification step.

[7] The process of any of [2] to [6] above, wherein the catalyst is at least one selected from the group consisting of chlorides of transition metals, magnesium, aluminum and tin.

[8] The process of any of [2] to [7] above, wherein the reaction between the allyl alcohol and hydrogen chloride is conducted under pressure.

BRIEF DESCRIPTION OF THE DRAWING

FIG. 1 is a graph showing the relationship between the allyl alcohol and hydrogen chloride molar concentration ratio $[AAL]^{1/2}/[HCL]$ in the reaction solution and the diallyl ether and allyl chloride molar ratio $[DAE]/[AC]$ produced by a reaction conducted at 85° C.

DETAILED DESCRIPTION OF THE INVENTION

The present invention will now be explained in further detail.

The allyl alcohol starting material used for the invention may be either anhydrous or in aqueous solution, and it is preferably used as a 70 wt % aqueous solution which is an azeotropic composition of water and allyl alcohol, as this is the cheapest available form.

The hydrogen chloride may also be used in anhydrous form or in aqueous solution with no problem, and it is preferably used as a 35 wt % aqueous solution from an economical standpoint.

The catalyst used for the reaction is preferably a compound containing at least one element selected from the group consisting of transition metals, Mg, Al and Sn. Here, a transition metal is an element with an atomic number of from 21 to 30 or an atomic number of from 39 to 48.

As representative compounds there may be mentioned copper (I) chloride, copper (II) chloride, palladium chloride, cobalt chloride, titanium tetrachloride, vanadium trichloride, nickel chloride, iron (III) chloride, aluminum chloride, magnesium chloride, tin tetrachloride and the like.

Metal oxides and hydroxides corresponding to these metal chlorides also act as chlorides in the presence of hydrogen chloride, and may be used as catalysts for the invention instead of these metal chlorides.

Preferred among these are copper (II) chloride, copper (I) chloride and palladium chloride from the standpoint of reaction yield, but there is no limitation to these. The catalyst is dissolved in a hydrogen chloride aqueous solution or in water and supplied to the reaction system.

Water is a by-product of the production of allyl chloride by the reaction. Water is also included when the starting materials for the reaction are used in the form of an aqueous solution. For continuous production of allyl chloride, therefore, it is necessary to draw off this surplus water.

However, when the reaction solution is drawn off directly, unreacted hydrogen chloride and the catalyst are also drawn out with the water that is drawn out. For an industrially economical reaction, then, it is necessary to separate and remove the excess water contained in the drawn out reaction solution, and restore the unreacted hydrogen chloride and catalyst back to the reaction system for reuse.

The excess water may usually be separated and removed by distillation. The organic components such as allyl chloride and allyl alcohol can also be separated out as low boiling point components along with the excess water, and at least a portion of these organic components may be returned to the reactor and/or to the allyl chloride purification step.

The hydrogen chloride and catalyst must be recovered as high boiling point components and reused, but in order to recover the hydrogen chloride as a high boiling point component, the hydrogen chloride is limited to approximately 20 wt % (under atmospheric pressure: 101.3 kPa), which is the maximum azeotropic composition as an aqueous solution with water $(HCL/(HCL+H_2O))$. Thus, the relationship between the water and hydrogen chloride in the reaction solution drawn out from the reactor must be such that the hydrogen chloride with the water minus the water by-product of the reaction and the water associated from the starting material is no greater than 20 wt % in terms of $HCL/(HCL+H_2O)$. In other words, when a large amount of water of 80% or greater excluding the catalyst is returned to the reaction system, this results in a major decrease in the concentration of the reaction starting materials, and the lower concentration of the starting materials leads to a lower reaction rate to allyl chloride.

This problem can be solved by carrying out the reaction at 80–120° C., preferably, and supplying the allyl alcohol and HCL to the reactor so that the molar concentration ratio of allyl alcohol and hydrogen chloride in the reactor $[AAL]^{1/2}/[HCL]$ is no greater than 0.2, as according to the present invention, thereby making it possible to suppress by-production of diallyl ether and obtain allyl chloride at a high yield. The reaction can usually be conducted at atmospheric pressure, and it may also be conducted under pressure for a reaction temperature of up to 120° C. If the reaction temperature is lower than 80° C., the reduced reaction rate will tend to lengthen the reaction time (residence time), which is undesirable in terms of productivity. It is preferably not higher than 120° C. as this can cause thermal decomposition of the allyl alcohol and allyl chloride.

The molar ratio of the allyl alcohol and hydrogen chloride supplied need only satisfy the condition that the molar concentration ratio of the allyl alcohol and hydrogen chloride $[AAL]^{1/2}/[HCL]$ in the reactor be no greater than 0.2, with combination of the reaction temperature and reaction time (residence time). The molar ratio AAL:HCL is preferably 1:1.5 to 1:5, and more preferably 1:2 to 1:3. If the supplied molar ratio of the hydrogen chloride with respect to the allyl alcohol is smaller than 1:1.5, the diallyl ether will tend to increase, and if it is larger than 1:5, the reaction rate will be improved but the supply volume of the hydrochloric acid solution will increase to an impractical level.

The allyl alcohol concentration in the reaction solution may be determined, for example, by an absolute calibration curve using high performance liquid chromatography. The analysis may be performed, for example, using a polymer-based distributing adsorption column for the column, and using an aqueous solution of acetonitrile:water=55:45 (by volume) as the eluant. The column temperature may be 50° C., the eluant flow rate 0.8 ml/min, and the detector a differential refractometer.

An azeotropic composition exists for the allyl chloride and water, and the azeotropic point is 43° C. at atmospheric pressure. An azeotropic composition also exists for the allyl alcohol starting material and the diallyl ether and water by-products, and the azeotropic point is 78° C. According to the invention, therefore, the unreacted allyl alcohol and the diallyl ether by-product will distill off with the allyl chloride. In order to prevent this, a distillation column or partial condenser may be provided on the reactor. This will allow the allyl chloride produced to substantially distill off with a distilling vapor temperature of preferably 35–85° C. and more preferably 43–78° C., and will allow the unreacted allyl alcohol and the diallyl ether by-product to be returned to the reactor.

The reaction solution drawn out from the reactor contains the catalyst, hydrogen chloride, allyl alcohol, allyl chloride, diallyl ether, water, etc.

It is necessary to separate the water from this mixture. The separation may generally be accomplished by distillation, and the distillation bottom liquid may be recovered and reused. The separated excess water contains allyl alcohol, allyl chloride and diallyl ether, and therefore it is further distilled and these components are recovered, with purification treatment if necessary, and eliminated from the system.

The hydrogen chloride concentration with respect to the water at this time is a maximum concentration of 20.2 wt %, which is the azeotropic composition with water at atmospheric pressure. When the metal chloride catalyst holds water of hydration, the water does not contribute to the azeotropy with hydrogen chloride, and therefore the hydrogen chloride is recovered with a dilution degree determined by the water held by the metal chloride. The concentration of the hydrogen chloride supplied to the reaction system and its molar ratio with respect to the allyl alcohol must be set with this in mind.

The allyl chloride-containing solution which is distilled off from the reaction system is obtained primarily as an azeotropic mixture of allyl chloride and water, and it comprises approximately 1 wt % of the reaction by-product diallyl ether, and approximately 2 wt % each of the unreacted allyl alcohol and hydrogen chloride. Also, since the solution separates into an aqueous phase and organic phase, a suitable means such as a phase separation tank may be used to separate the organic phase from the aqueous phase. The separated aqueous phase contains allyl chloride, allyl alcohol and hydrochloric acid, and therefore it may be supplied directly to the reactor and/or recovered after mixing with the drawn out reaction solution and separating the water, to allow reuse of these compounds.

The hydrogen chloride in the separated organic phase is preferably removed since it is a cause of corrosion of the equipment. A common method of removing hydrogen chloride is neutralization with an alkali aqueous solution, but using such a method is not preferred because the neutralized organic phase will contain chloride salts, and precipitation of these chlorides can cause clogging of the distillation column used for purification of the allyl chloride.

According to the process of the invention it is possible to remove the hydrogen chloride in the organic phase by extraction of the organic phase with water, without producing salts, thereby solving the problem of salt precipitation. The extraction may be accomplished by a method of combining an agitation tank and a phase separation tank in a continuous multistage manner, or a method of using an extraction column in which water is supplied from the top end and the organic phase is supplied from the lower end, and any such type of extraction method may be used. The weight ratio of the organic phase and the water used for extraction is preferably $1/100$ to $1/2$ (weight ratio) and more preferably $1/50$ to $1/10$ (weight ratio), as the water/organic phase ratio. The aqueous phase after extraction will contain allyl alcohol and allyl chloride in addition to hydrogen chloride, and therefore after the extraction it may be mixed with the drawn out reaction solution and the separated water, before recovery to the reactor for reuse. If the water/organic phase ratio is smaller than $1/100$, the removal rate of the hydrogen chloride may be reduced, and if it is larger than $1/2$, the amount of water used for extraction will be excessively large, which is undesirable as it will require excessive equipment for recovery of the hydrogen chloride, allyl alcohol and allyl chloride from the extracted aqueous phase after extraction.

After removal of the hydrochloric acid, the organic phase may be distilled and purified to obtain a high purity allyl chloride product. Here, the allyl alcohol, diallyl ether and the non-product allyl chloride, which are separated by distillation, may be returned to the reactor and reused.

The present invention will now be explained in greater detail by way of examples and comparative examples, with the understanding that the invention is in no way limited thereby.

EXAMPLE 1

A copper (II) chloride-containing hydrochloric acid aqueous solution and a 70% allyl alcohol aqueous solution were continuously supplied to a flask (500 ml) equipped with a stirrer and distillation column, and the reaction solution was continuously drawn out with a pump to maintain a constant liquid level of the reaction solution in the flask. The distillation column had an inner diameter of 20 mm$\phi$ and 5$\phi$×10 mm ceramic Raschig rings filled to 40 ml.

A copper (II) chloride-containing hydrochloric acid aqueous solution, comprising 15.1 wt % copper (II) chloride, 20.4 wt % hydrogen chloride and 74.5 wt % water, was supplied at 18.5 g/min, and a 70 wt % allyl alcohol aqueous solution was supplied at 3.54 g/min. The liquid amount supplied to the reactor was a total of 22.04 g/min, with 11.2 wt % AAL, 17.1 wt % hydrogen chloride, 2.7 wt % copper (II) chloride, allyl alcohol:hydrochloric acid=1:2.4 (moles) and allyl alcohol:copper (II) chloride=1:0.5 (moles). The oil bath was heated to a reaction temperature of 95° C. The draw-out rate was adjusted with a pump to maintain a reaction solution volume of 330 ml based on the liquid level. The residence time was about 23 minutes. Stripping and drawing out of the reaction solution were continued for 3 hours, and after confirming the stripping gas temperature and reaction solution composition and determining that the system was stable, the data was recorded for one hour. The distillation fraction was 192 g/hour, and the draw-out rate of the reaction solution was 1130 g/hour.

The distillation fraction comprised 97.7 wt % of an organic phase and 2.3 wt % of an aqueous phase. The organic phase contained 98.0 wt % allyl chloride, with 0.98 wt % allyl alcohol, 0.56 wt % diallyl ether and 0.10% hydrogen chloride. The drawn out reaction solution contained 0.15 wt % allyl chloride, 0.39 wt % allyl alcohol, 0.006 wt % diallyl ether and 14.6 wt % hydrogen chloride.

The allyl chloride was produced at 3.09 g/min, the yield of AC with respect to the supplied AAL was 94.7% (moles of AC produced/moles of AAL supplied), and the AC selectivity was 98.9% (moles of AC produced/moles of AAL reacted). Diallyl ether was produced at 0.019 g/min, and the yield of DAE with respect to the supplied AAL was 0.9% (moles of DAE produced×2/moles of AAL supplied). The molar concentration ratio of allyl alcohol and hydrogen chloride $[AAL]^{1/2}/[HCL]$ in the drawn out reaction solution was 0.057, and the molar ratio of DAE to AC [DAE]/[AC] produced by the reaction was 0.0047.

EXAMPLE 2

The same reaction apparatus was used as in Example 1 for the same reaction, using copper (II) chloride as the catalyst. The flow rate of the total liquid supplied to the reactor, the composition of hydrogen chloride, copper (II) chloride and allyl alcohol, the molar ratio of AAL to HCL supplied, the molar ratio of AAL and $CuCl_2$, the reaction temperature and the reaction time (residence time) were as shown in Table 1. Tables 2 and 3 show the flow rate of the reaction distillation fraction, the proportion of the organic phase in the distillation fraction, the composition of the organic phase, the draw-out rate of the reaction solution and the reaction solution composition. Also, Table 4 shows the reaction results, i.e. the yield of AC with respect to the supplied AAL (moles of AC produced/moles of AAL supplied), the AC selectivity (moles of AC produced/moles of AAL reacted), the DAE yield with respect to the supplied AAL (moles of DAE produced×2/moles of AAL supplied), the molar concentration ratio of AAL and HCL $[AAL]^{1/2}/[HCL]$ in the drawn out reaction solution, and the molar ratio of DAE to AC [DAE]/[AC] produced by the reaction.

EXAMPLE 3

A glass autoclave (500 ml) equipped with a stirrer and a distillation column comprising a pressure-resistant glass tube filled with 40 ml of 5φ×10 mm ceramic Raschig rings was used for reaction under pressure. The gas used to draw out the distillation column was controlled for a reaction temperature of 120° C. The reaction conditions and reaction results are shown in Tables 1 to 4.

EXAMPLES 4–6, COMPARATIVE EXAMPLES 1–4

A reaction was conducted in the same manner as Example 1 with the reaction conditions shown in Table 1. The results are shown in Tables 2 to 4.

TABLE 2

| | Reaction distillation fraction flow rate g/min | Organic layer wt % | AC wt % | AAL wt % | DAE wt % |
|---|---|---|---|---|---|
| | | Organic layer composition | | | |
| Example 1 | 3.19 | 97.7% | 98.0% | 0.98% | 0.56% |
| Example 2 | 2.12 | 97.8% | 98.1% | 1.1% | 0.33% |
| Example 3 | 3.15 | 98.0% | 98.3% | 1.2% | 0.18% |
| Example 4 | 5.21 | 96.9% | 92.7% | 4.9% | 1.6% |
| Example 5 | 3.01 | 97.3% | 97.2% | 1.5% | 0.80% |
| Example 6 | 4.72 | 95.3% | 93.7% | 4.3% | 1.2% |
| Comp. Ex. 1 | 2.07 | 96.6% | 86.4% | 2.7% | 10.2% |
| Comp. Ex. 2 | 3.98 | 96.0% | 96.6% | 6.2% | 6.1% |
| Comp. Ex. 3 | 2.68 | 97.0% | 96.0% | 1.7% | 2.1% |
| Comp. Ex. 4 | 2.27 | 96.9% | 97.2% | 1.4% | 1.1% |

TABLE 3

| | Drawn out reaction solution composition | | | |
|---|---|---|---|---|
| | Draw-out flow rate g/min | AC wt % | AAL wt % | DAE wt % | HCL wt % |
| Example 1 | 18.8 | 0.15% | 0.39% | 0.006% | 14.6% |
| Example 2 | 12.5 | 0.17% | 0.26% | 0.005% | 14.0% |
| Example 3 | 18.6 | 0.10% | 0.22% | 0.002% | 13.9% |
| Example 4 | 29.9 | 1.01% | 1.81% | 0.02% | 11.9% |
| Example 5 | 20.6 | 0.87% | 0.99% | 0.03% | 14.7% |
| Example 6 | 30.9 | 0.50% | 0.62% | 0.02% | 15.6% |
| Comp. Ex. 1 | 33.1 | 0.66% | 15.6% | 0.18% | 3.81% |
| Comp. Ex. 2 | 30.8 | 0.80% | 8.35% | 0.08% | 6.0% |
| Comp. Ex. 3 | 32.3 | 0.63% | 3.57% | 0.03% | 11.9% |

TABLE 1

| | Supply rate g/min | AAL wt % | HCL wt % | $CuCl_2$ wt % | HCL/AAL mol/mol | $CuCl_2$/AAL mol/mol | Reaction temperature | Residence time min |
|---|---|---|---|---|---|---|---|---|
| Example 1 | 22.04 | 11.2% | 17.1% | 12.7% | 2.4 | 0.5 | 95 | 23 |
| Example 2 | 14.64 | 11.2% | 17.2% | 12.7% | 2.5 | 0.5 | 100 | 22 |
| Example 3 | 21.85 | 11.2% | 17.3% | 12.7% | 2.5 | 0.5 | 120 | 23 |
| Example 4 | 35.13 | 13.3% | 16.8% | 15.5% | 2.0 | 0.5 | 85 | 11 |
| Example 5 | 23.62 | 11.0% | 17.7% | 12.7% | 2.6 | 0.5 | 85 | 15 |
| Example 6 | 35.63 | 10.6% | 17.3% | 12.8% | 2.6 | 0.5 | 95 | 11 |
| Comp. Ex. 1 | 35.12 | 19.4% | 6.4% | 23.3% | 0.5 | 0.5 | 85 | 10 |
| Comp. Ex. 2 | 34.74 | 16.6% | 10.3% | 19.2% | 1.0 | 0.5 | 85 | 11 |
| Comp. Ex. 3 | 34.98 | 9.5% | 14.8% | 10.9% | 2.5 | 0.5 | 85 | 11 |
| Comp. Ex. 4 | 30.00 | 10.3% | 16.6% | 12.0% | 2.6 | 0.5 | 75 | 16 |

TABLE 3-continued

| | Drawn out reaction solution composition | | | | |
|---|---|---|---|---|---|
| | Draw-out flow rate g/min | AC wt % | AAL wt % | DAE wt % | HCL wt % |
| Comp. Ex. 4 | 27.7 | 0.90% | 4.20% | 0.08% | 13.6% |

TABLE 4

| | AC yield % | AC selectivity % | DAE yield % | $AAL^{1/2}/HCL$ $(mol/l)^{1/2}/$ mol/l | DAE/AC mol/mol |
|---|---|---|---|---|---|
| Example 1 | 94.7% | 98.9% | 0.9% | 0.057 | 0.0047 |
| Example 2 | 95.2% | 98.5% | 0.5% | 0.048 | 0.0028 |
| Example 3 | 94.7% | 97.8% | 0.3% | 0.045 | 0.0015 |
| Example 4 | 80.7% | 97.0% | 2.1% | 0.15 | 0.013 |
| Example 5 | 88.8% | 98.2% | 1.3% | 0.090 | 0.0074 |
| Example 6 | 87.5% | 97.3% | 1.8% | 0.067 | 0.010 |
| Comp. Ex. 1 | 21.6% | 91.9% | 4.6% | 1.38 | 0.106 |
| Comp. Ex. 2 | 46.7% | 90.9% | 5.2% | 0.64 | 0.056 |
| Comp. Ex. 3 | 61.5% | 96.0% | 2.3% | 0.21 | 0.019 |
| Comp. Ex. 4 | 58.8% | 96.2% | 1.8% | 0.20 | 0.015 |

EXAMPLE 7

Continuous extraction was performed with water using the organic phase obtained in Example 1. The continuous extraction apparatus used was a glass tube having a 40 mm inner diameter, equipped with a liquid supply nozzle and overflow nozzle at the upper end, a liquid supply nozzle at the lower end and a liquid draw-out nozzle at the bottom, and filled to a filled layer height of 500 mm with 5φ×10 mm ceramic Raschig rings. Purified water was supplied from the upper end at 60 g/hour while an organic phase containing 0.1 wt % hydrogen chloride was supplied from the lower end at 1200 g/hour, and the organic phase and aqueous phase were drawn out until the interface between the organic phase and the aqueous phase reached 50% of the filled layer. After continuous extraction in this state for 3 hours, the organic phase and aqueous phase were recovered, and the hydrogen chloride concentration was measured. The hydrogen chloride concentration of the organic phase was less than 50 ppm, and the hydrogen chloride concentration of the aqueous phase was 1.9 wt %.

EXAMPLE 8

The same reaction apparatus as Example 1 was used for a reaction, supplying the drawn out reaction solution to an organic matter recovery column, recovering the organic matter from the top and returning it to the reactor, supplying the column bottom solution to a hydrochloric acid/catalyst recovery column, separating the water from the top, and recovering the hydrochloric acid and catalyst from the column bottom and returning them to the reactor.

The reaction conditions were, reaction temperature: 100° C., residence time in reactor: 20 minutes, catalyst: copper (II) chloride, allyl alcohol:hydrogen chloride=1:3.0 (moles), and allyl alcohol:catalyst=1:0.5 (moles). Also, the organic matter recovery column was operated under atmospheric pressure, and the solution at the top of the column was drawn out with a column top temperature of 94–95° C. The hydrochloric acid/catalyst recovery column was also operated under atmospheric pressure, and the solution at the top of the column was drawn out with a column top temperature of 108–112° C. As a result, the yield of allyl chloride distilled off from the reactor was 96.4%. The concentration of hydrogen chloride returned to the reactor from the hydrochloric acid/catalyst recovery column was 18.2% with respect to the water.

According to the process of the invention it is possible to obtain allyl chloride at a higher yield and in a more economical and advantageous manner than by prior art processes.

We claim:

1. An allyl chloride production process that comprises a) a step of supplying allyl alcohol and hydrogen chloride to a reactor and reacting them to produce allyl chloride and water, b) a step of distilling the produced allyl chloride out of the reaction system by a vapor phase and recovering it, c) a step of drawing out the reaction solution from the reactor, d) a step of distilling and separating the water from the drawn out reaction solution, and e) a step of returning, back to the reactor, the remaining solution containing the hydrochloric acid and catalyst from which the water has been distilled off and separated.

2. An allyl chloride production process whereby allyl alcohol and hydrogen chloride are reacted in the presence of a catalyst and the resulting allyl chloride is distilled off from the reaction system, wherein the allyl chloride production process comprises conducting the reaction in a range of 80–120° C. and supplying the allyl alcohol and hydrogen chloride such that the molar concentration ratio of the allyl alcohol and hydrogen chloride in the reaction solution is no greater than 0.2 in terms of $[allyl\ alcohol]^{1/2}/[hydrogen\ chloride]$.

3. The process of claim 2, wherein the organic phase containing the distilled allyl chloride is separated from the aqueous phase, and the organic phase is distilled off after extraction using water.

4. The process of claim 2, wherein at least a portion of the aqueous phase separated from the organic phase and/or an aqueous extract of the organic phase is returned to the reactor.

5. The process of claim 2, which further comprises the following three steps:

(1) A step of drawing out the reaction solution from the reactor;

(2) A step of distilling off and separating the water from the reaction solution obtained in step (1);

(3) A step of returning, to the reactor, the remaining solution containing the hydrochloric acid and catalyst, obtained in step (2).

6. The process of claim 5, wherein during distillation and separation of the water in step (2), the fraction with a lower boiling point than water is recovered and at least a portion of this fraction is returned to the reactor and/or the allyl chloride purification step.

* * * * *